(12) United States Patent
Goldshtein et al.

(10) Patent No.: US 8,497,491 B2
(45) Date of Patent: Jul. 30, 2013

(54) AIR STERILIZING ASSEMBLY

(75) Inventors: Yakov Abrammerovich Goldshtein, Moscow (RU); Sergei Gennadevich Shashkovsky, Moscow (RU)

(73) Assignee: Yanex Intellectual Property Limited, Nicosia (CY)

( * ) Notice: Subject to any disclaimer, the term of this patent is extended or adjusted under 35 U.S.C. 154(b) by 0 days.

(21) Appl. No.: 13/321,168

(22) PCT Filed: Aug. 13, 2009

(86) PCT No.: PCT/RU2009/000402
§ 371 (c)(1),
(2), (4) Date: Jan. 26, 2012

(87) PCT Pub. No.: WO2010/134838
PCT Pub. Date: Nov. 25, 2010

(65) Prior Publication Data
US 2012/0119108 A1    May 17, 2012

(30) Foreign Application Priority Data

May 20, 2009   (RU) ................................ 2009118837

(51) Int. Cl.
*H01J 17/34* (2006.01)
*H01J 17/28* (2006.01)

(52) U.S. Cl.
USPC .... 250/504 R; 250/436; 250/438; 250/455.1; 250/461.1; 315/53; 315/209 CD; 313/22; 313/24; 313/231.61; 313/324; 313/493; 362/373; 362/218; 362/294; 362/217.01

(58) Field of Classification Search
USPC ................ 250/436, 438, 455.1, 493.1, 461.1, 250/472.1, 473.1, 504 R; 315/50–53, 56–59, 315/209 CD, 275, 355; 362/216, 217.01, 362/218, 226, 257, 264, 294, 310, 363, 373; 422/22, 24, 120, 121, 186, 186.11, 186.19, 422/186.2, 186.25
See application file for complete search history.

(56) References Cited

U.S. PATENT DOCUMENTS 4,045,680 A     8/1977   Loher
4,300,073 A *  11/1981   Skwirut et al. .................. 315/53
(Continued)

FOREIGN PATENT DOCUMENTS

EP     0220050 A2    4/1987
GB     1013990 A     12/1965
(Continued)

OTHER PUBLICATIONS

Extended European search report, Application No. /Patent No. 09844998.6-0113 / 2433657 (PCT/RU2009/000402), dated Dec. 19, 2012, 6 pages.

(Continued)

*Primary Examiner* — Bernard E Souw
(74) *Attorney, Agent, or Firm* — Baker & McKenzie LLP

(57) ABSTRACT

An air disinfection device aimed at improving the efficiency and quality of air disinfection or sterilization may be achieved through an air disinfection device comprising a body housing a power supply and control unit, which, in turn, comprises an energy storage capacitor, a high-voltage constant current source, an ignition pulse generator, a ferrite-core pulse transformer, and a program control unit. The air disinfection device may also comprise an ultra-violet radiation source in the form of a pulsed gas-discharge lamp mounted on the body and enclosed in a tubular quartz casing. Given that the energy storage capacitor and the pulsed gas-discharge lamp may form a discharge circuit connected to the ignition pulse generator through the ferrite-core pulse transformer, the pulsed gas-discharge lamp may be placed in a bactericidal radiation translucent casing, resulting in convection air-cooling due to a natural draft inside the casing that disinfects and sterilizes surrounding air.

8 Claims, 3 Drawing Sheets

U.S. PATENT DOCUMENTS

| | | | |
|---|---|---|---|
| 4,503,360 A | | 3/1985 | Bedel |
| 4,806,768 A | | 2/1989 | Keutenedjian |
| 5,537,301 A | | 7/1996 | Martich |
| 5,943,970 A | * | 8/1999 | Gonopolsky et al. ......... 110/346 |
| 6,679,068 B1 | | 1/2004 | Guzorek |
| 2002/0033327 A1 | * | 3/2002 | Benda et al. ............... 204/158.2 |
| 2004/0120844 A1 | * | 6/2004 | Tribelsky et al. ................. 422/2 |
| 2004/0144733 A1 | * | 7/2004 | Cooper et al. ................ 210/748 |

FOREIGN PATENT DOCUMENTS

| | | |
|---|---|---|
| JP | 10323558 A | 12/1998 |
| RU | 94018873 A1 | 4/1996 |
| RU | 2092191 C1 | 10/1997 |
| RU | 2153886 C1 | 8/2000 |

OTHER PUBLICATIONS

International Search Report (English translation), PCT/RU2009/000402, dated Jan. 28, 2010, 1 page.

International Preliminary Report on Patentability and Written Opinion (English translation), PCT/RU2009/000402, dated Nov. 29, 2011, 6 pages.

* cited by examiner

AIR STERILIZING ASSEMBLY

TECHNICAL FIELD

The disclosed embodiments relate to medical equipment, and more specifically, to equipment that can be used to improve the efficiency of disinfecting or sterilizing air in various rooms used for different purposes.

BACKGROUND OF THE INVENTION

Air disinfection/sterilizing devices may include one or more sources of ultra-violet radiation in the form of mercury gas-discharge bactericidal lamps and operating in a continuous lighting mode (for example, RU 2153886 C1, A61L9/20, 2000; RU 2153886 C1, A61L9/20, 2007; or EP 0220050, A61L9/18, 1987). One disadvantage of these devices is low productivity, which is caused by low intensity monochromatic radiation that is emitted from the bactericidal lamps, and, as a result, contributes to needing longer exposure periods to ensure effective air disinfection.

Another device used for air disinfection and deodorization contains a body housing a power supply and control unit, which, in turn, includes an energy storage capacitor, a high-voltage constant current source, an ignition pulse generator, a ferrite-core pulse transformer, and a control circuit, together with an ultra-violet source in the form of a pulsed gas-discharge lamp mounted on the body and enclosed in a tubular quartz casing. The unit is cooled by water, wherein the energy storage capacitor and the gas-discharge lamp form a discharge circuit, connected to the ignition pulse generator through the ferrite-core pulse transformer (RU 2092191 C1, A61L9/20, 1997). The water cooling system used in a pulsed gas-discharge lamp complicates design, increases the weight of construction, and reduces the efficiency of air disinfection processes.

SUMMARY OF THE INVENTION

An aspect of the disclosed embodiments is aimed at simplifying the design of a device for improving the efficiency and quality of air disinfection or sterilization. An embodiment of the air disinfection device of the present disclosure may contain a body housing a power supply and control unit, which, in turn, includes an energy storage capacitor and a high-voltage constant current source. This device may also contain an ignition pulse generator, a ferrite-core pulse transformer, and a program control unit, together with an ultra-violet radiation source in the form of a pulsed gas-discharge lamp mounted on the body and enclosed in a tubular quartz casing. Given that the energy storage capacitor and the pulsed gas-discharge lamp may form a discharge circuit connected to the ignition pulse generator through the ferrite-core pulse transformer, the pulsed gas-discharge lamp may be placed in a bactericidal radiation translucent casing, with an option of convective air-cooling due to a natural draft inside the casing.

In addition, there may be one or more orifices in an upper level of the casing and one or more orifices in a lower level of the casing according to the following ratio of parameters of Ratio (1):

$$h \cdot \frac{S_{upper}^2 \cdot S_{lower}^2}{S_{upper}^2 + S_{lower}^2} = \frac{1}{A} \cdot C^2 U_0^4 F^2$$

wherein:

h is the distance between the orifices of the upper and lower levels, in meters (m);

$S_{upper}$ is the total surface area of the orifices in the upper level, in m$^2$;

$S_{lower}$ is the total surface area of the orifices in the lower level, in m$^2$;

A=(2 to 30)·10$^{13}$ J$^2$/m$^5$ s$^2$, wherein A is the power correlation coefficient;

C is the capacitance of energy storage capacitor, in farads (F);

$U_0$ is the charge voltage of the energy storage capacitor, in volts (V); and

F is the pulse repetition rate of the ignition pulse generator, in hertz (Hz).

It may be preferable for the ultra-violet radiation source to be installed vertically on the body, and the pulsed gas-discharge lamp may be U-shaped or cylindrical. Furthermore, the orifices in the lower level may be made on the lateral surface of the casing. In addition, the ultra-violet radiation source may be mounted horizontally, and the orifices in both the upper and lower levels may be made on the lateral surface of the casing.

Providing a casing with orifices in the upper and lower levels may allow convection cooling of the pulsed gas-discharge lamp through ascending air flow, which passes through the casing as natural air draft. This may simplify the design of the source of ultra-violet radiation and the device as a whole. The aforementioned Ratio (1), which includes the power correlation coefficient and associated structural and power (operating) parameters of the unit, and which may be achieved through experimentation, may ensure that the range of A=(2 to 30)·10$^{13}$ J$^2$/m$^5$ s$^2$ and will provide both optimal and efficient natural convection and cooling of the pulsed gas-discharge lamp, and ozone formation from oxygen in the air thanks to short-wave ultra-violet radiation and thermal disintegration of ozone due to heat emitted through pulsed electric discharges in the gas-discharge lamp. This may enable the device to function reliably and may ensure a high degree of air disinfection and a low level of ozone production in the processed premises.

DETAILED DESCRIPTION

Figure 1:
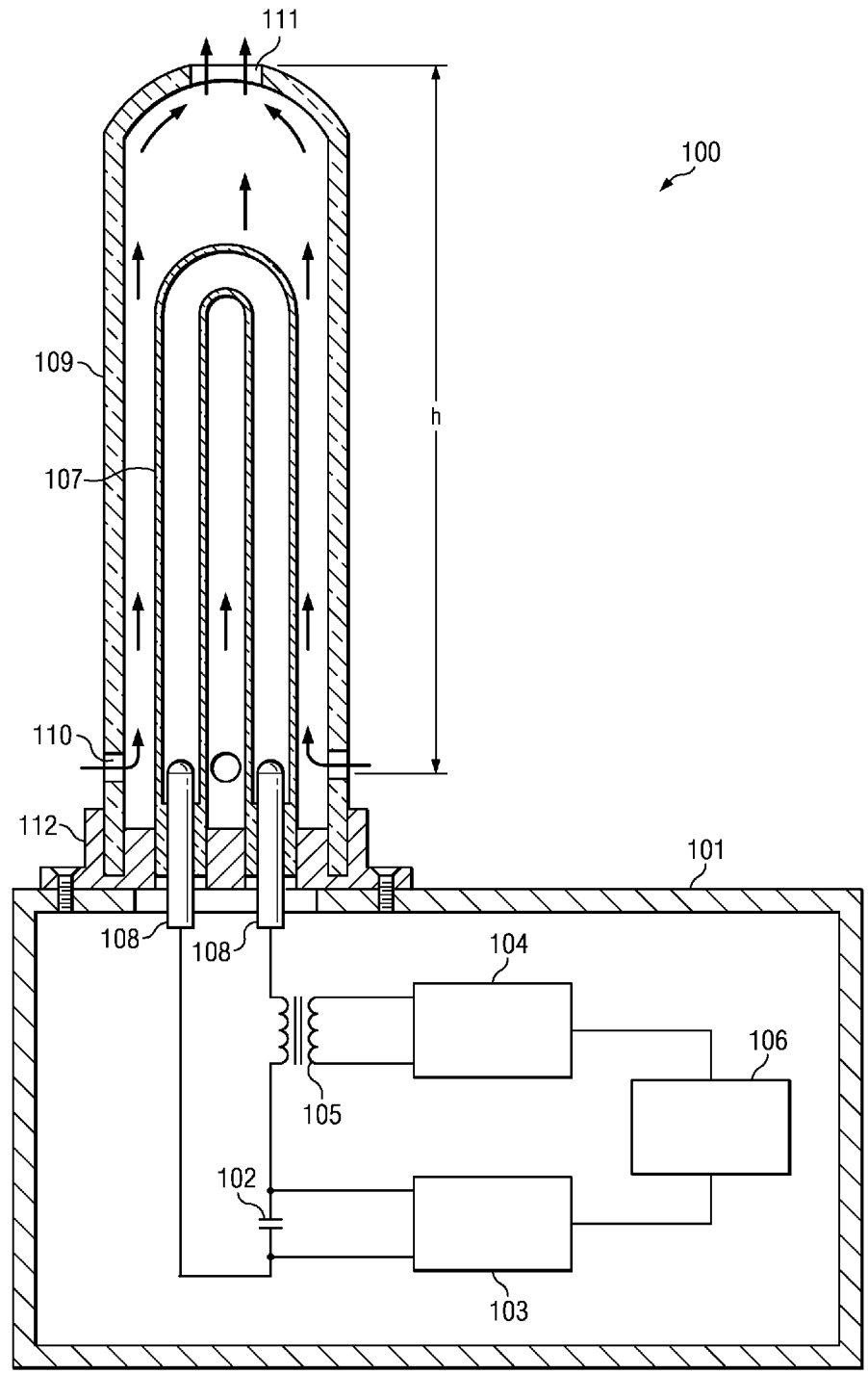
FIG. 1 depicts a profile view of an air disinfection device with a vertical U-shaped gas-discharge lamp, in accordance with one embodiment of the present disclosure.

FIG. 1 depicts a profile view of an air disinfection device 100 with a vertical U-shaped gas-discharge lamp, in accordance with one embodiment of the present disclosure. The air disinfection device 100 may comprise a body 101 housing a power supply and control unit. The control unit may comprise an energy storage capacitor 102 connected to a high-voltage constant current source 103, an ignition pulse generator 104 connected to a ferrite-core pulse transformer 105, and a program control unit 106. The source of ultra-violet radiation may be in the form of a pulsed gas-discharge lamp 107 comprising the energy storage capacitor 102, and a secondary winding of the ferrite-core pulse transformer 105 in a closed discharge circuit may be mounted on the body 101.

Figure 2:
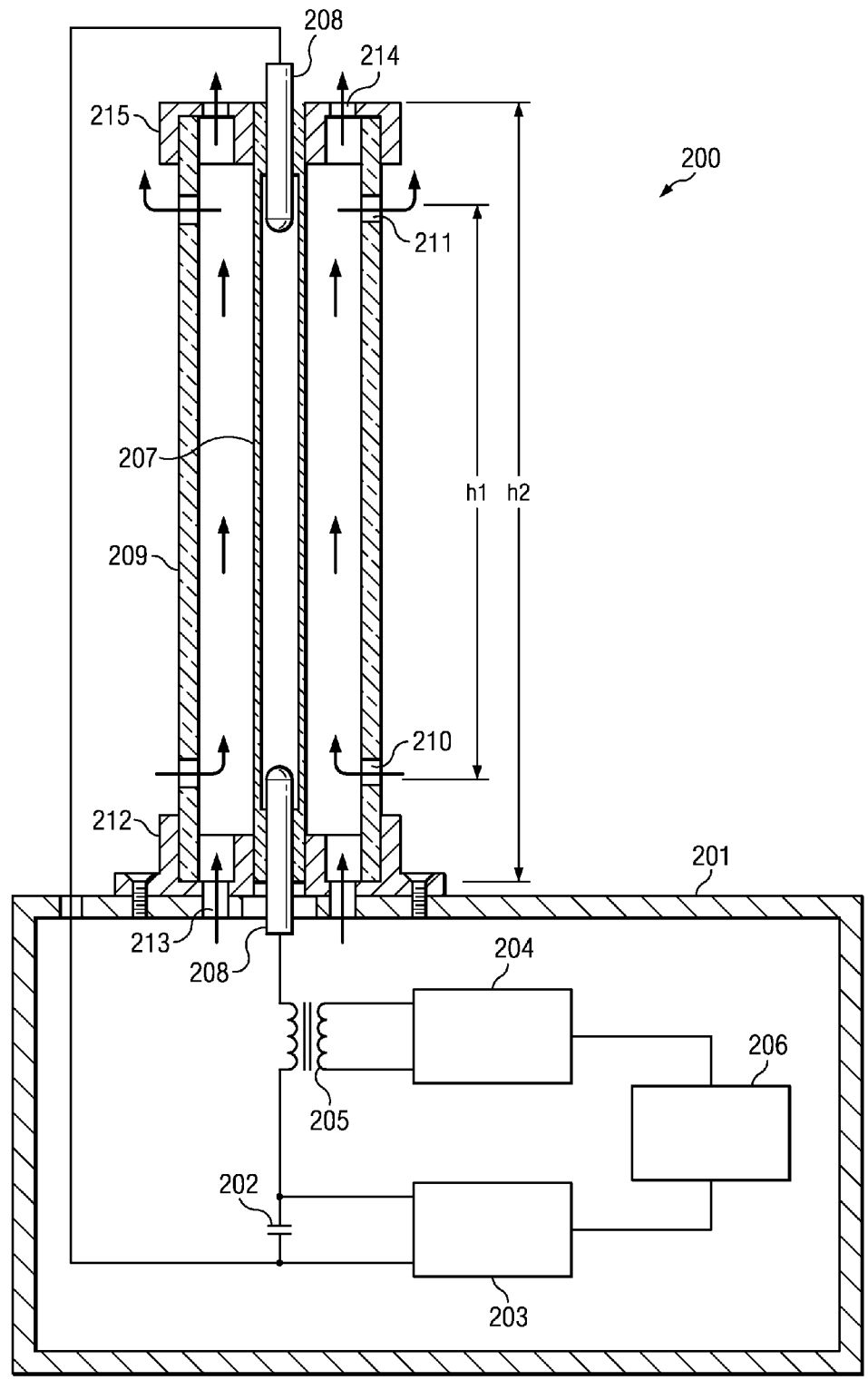
FIG. 2 depicts a profile view of an air disinfection device with a vertical cylindrical gas-discharge lamp, in accordance with one embodiment of the present disclosure.

FIG. 2 depicts a profile view of an air disinfection device 200 with a vertical cylindrical gas-discharge lamp, in accordance with one embodiment of the present disclosure. The air disinfection device 200 may comprise a body 201 housing a power supply and control unit. The control unit may comprise an energy storage capacitor 202 connected to a high-voltage constant current source 203, an ignition pulse generator 204 connected to a ferrite-core pulse transformer 205, and a program control unit 206. The source of ultra-violet radiation may be in the form of a pulsed gas-discharge lamp 207 comprising the energy storage capacitor 202, and a secondary winding of the ferrite-core pulse transformer 205 in a closed discharge circuit may be mounted on the body 201.

The pulsed gas-discharge lamp may be in the form of a quartz U-shaped tube, as shown in element 107 in FIG. 1, or in a cylindrical form, as shown in element 207 in FIG. 2, having a cavity filled with inert Xenon gas at a pressure measuring between 300 and 450 Torr. The pulsed gas-discharge lamp 107, 207 may be proximate to one or more welded electrodes 108, 208 located at the end poles. The welded electrodes 108, 208 may be made from thoriated tungsten and may be enclosed in a bactericidal radiation translucent casing 109, 209. The welded electrodes 108, 208, for example, may be made from fused quartz, whose spectral transparency range usually varies from 185 to 2,700 nm, or may be made from sapphire.

If the pulsed gas-discharge lamp 107 has a U-shaped tube, as shown in FIG. 1, the casing 109 may comprise one or more orifices. The casing 109 may have one or more orifices 110 in the lower level and one or more orifices 111 in the upper level, wherein the distance between the orifices 110, 111 equals "h," as shown in FIG. 1. The casing 109 and the pulsed gas-discharge lamp 107 may be preferably mounted in a vertical position on the body 101 by means of a dielectric flange 112.

If the pulsed gas-discharge lamp 207 has a straight cylinder shape, as shown in FIG. 2, the casing 209 may comprise one or more orifices. The casing 209 may have one or more orifices 211 in the upper level and one or more orifices 210 in the lower level on the lateral surface of the cylindrical casing 9, wherein the distance between the orifices 210, 211 equals "$h_1$". It may also be possible to place one or more lower-level orifices 213 in a lower dielectric flange 212, and one or more upper-level orifices 214 in an upper dielectric flange 215, wherein the distance between orifices 213, 214 equals "$h_2$".

Figure 3:
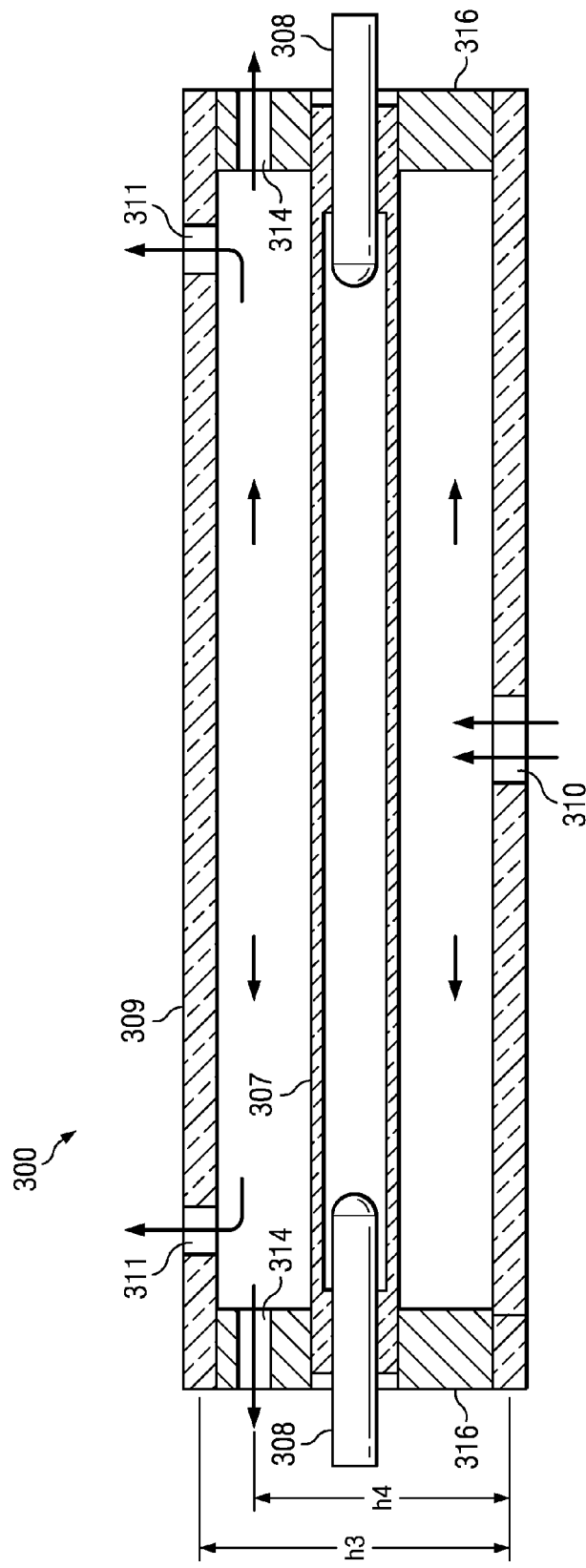
FIG. 3 depicts a pulsed gas-discharge lamp in a horizontal arrangement, in accordance with one embodiment of the present disclosure.

FIG. 3 depicts a design of a pulsed gas-discharge lamp 300 in a horizontal arrangement, in accordance with one embodiment of the present disclosure. In FIG. 3, a pulsed gas-discharge lamp 307 may be horizontally fixed on a casing 309 and may have one or more lower-level orifices 310, which may be made in the middle of the lower part of the lateral surface of the casing 309, and one or more upper-level orifices 311, which may be made in the upper part of the lateral surface of the casing 309, closer to the end poles, wherein the distance between orifices 310, 311 equals "$h_3$". In addition, or alternatively, the casing 309 may have one or more orifices 314 in dielectric flanges 316, wherein the distance between orifices 314 equals "$h_4$". One or more electrodes 308 may extend from the dielectric flanges 316 and from the casing 309.

The air disinfection devices 100, 200, 300 may be featured by Ratio (1), associating designed geometrical parameters of the casing 109, 209, 309 and power (operational) parameters for using the pulsed gas-discharge lamp 107, 207, 307 of Ratio (1):

$$h \cdot \frac{S_{upper}^2 \cdot S_{lower}^2}{S_{upper}^2 + S_{lower}^2} = \frac{1}{A} \cdot C^2 U_0^4 F^2$$

wherein:

h is the distance between the orifices of the upper and lower levels, in meters (m);

$S_{upper}$ is the total surface area of the orifices in the upper level, in m$^2$;

$S_{lower}$ is the total surface area of the orifices in the lower level, in m$^2$;

A=(2 to 30)·10$^{13}$ J$^2$/m$^5$ s$^2$, wherein A is the power correlation coefficient;

C is the capacitance of energy storage capacitor, in farads (F);

$U_0$ is the charge voltage of the energy storage capacitor, in volts (V); and

F is the pulse repetition rate of the ignition pulse generator, in hertz (Hz).

The aforementioned range A=(2 to 30)·10$^{13}$ J$^2$/m$^5$ s$^2$ may provide for both optimal and efficient flowing processes of natural convection in the casing 109, 209, 309, and cooling of the pulsed gas-discharge lamp 107, 207, 307. The range A=(2 to 30)·10$^{13}$ J$^2$/m$^5$ s$^2$ may also provide for the processes of ozone formation from oxygen in the air due to short-wave ultra-violet radiation and thermal disintegration of ozone due to heat emitted through electric pulse discharges in the gas-discharge lamp 107, 207, 307. These processes may enable the pulsed gas-discharge lamp 107, 207, 307 to function reliably, while ensuring a high degree of air disinfection or sterilization and a low level of ozone production in the processed premises.

Calibrated results of microbiological tests may be entered into the program control unit 106, 206, 306. These tests may define irradiation periods required in specific spaces of the premises to attain required bactericidal efficiency and good quality air disinfection in order to assign particular technical parameters, corresponding to the Ratio (1).

In an embodiment, the air disinfection devices 100, 200, 300 may operate in the following manner, with numerals referencing elements shown in FIG. 1, although like elements in FIGS. 2 and 3 may perform like functionality:

Before actual work operations may be initiated, the device may be installed in the middle of a room, the operator may enter data about the space (volume) of the room and required disinfection levels into the program control unit 106, and then the operator may switch on the device and leave the room.

After a set delay time, for example, 20 to 30 seconds, the program control unit 106 may switch on the constant current high-voltage source 103, which charges the energy storage capacitor 102. After reaching the required voltage, for example $U_0$=1.4 to 2.8 kV, the control circuit 106 may switch off the constant current high-voltage source 3 and start the ignition pulse generator 104. The ignition pulse generator may produce impulses voltages of 0.7 to 1.5 kV for durations of 0.1 to 1.0 μs, generating a corresponding current in the primary winding of the pulse transformer 105. Because the two windings are electromagnetically coupled through the common ferrite core, impulse voltages up to 20 kW may be induced in the secondary winding of the pulse transformer 105. This voltage may be applied across electrodes 108 and may cause primary electric breakdown of Xenon gas in the cavity of the pulsed gas-discharge lamp 107. The energy storage capacitor 102 may the discharge the gas through a conductive plasma channel. Then, this primary plasma may be strongly ionized, heated up, and expanded, filling up all the internal space of the cavity of the pulsed gas-discharge lamp 107. Plasma temperatures may reach 12,000 to 18,000 K at the peak of the discharge current pulse. Such optically dense plasma may emit a strong ultra-violet and visible radiation with a continuous spectrum completely covering the bactericidal radiation range, for example, from 205 to 305 nm. This radiation may pass through a bactericidal radiation translucent tube of the pulsed gas-discharge lamp 107 and the casing 109, reaching the surrounding air space of the room and disinfecting the area.

After the energy storage capacitor 102 is discharged, the current may stop flowing through the plasma. The plasma may cool down, become de-ionized, and may return to its usual molecular state. Next, the process may be repeated at the rate defined by the power of the high-voltage constant current source 103, for example, F=2 to 4 Hz. The device 100 may switched off when the determined time for processing has been terminated.

Discharge current impulses and, correspondingly, radiation impulses may be repeated as a periodic sequence. A half-amplitude width of the impulse current may be 80 to 120 μsec, whereas the impulse repetition period may range from 300 to 500 msec. That is, the energy reserved in the energy storage capacitor may be injected into the plasma for a very short time, namely 3,000 to 5,000 times less than the inter-impulse time.

Each ultra-violet radiation impulse, and more exactly, the ultra-violet radiation with a wavelength less than 210 nm, may cause formation of some air-derived ozone in the space between the casing 109 and the pulsed gas-discharge lamp 107. This ozone may not make its way immediately into the surrounding environment, as it may be held back by the casing 109, which would then requires a considerable amount of time to exit spontaneously through the orifices in the casing 109.

As the device 100 continues to work, the air/ozone mixture in the space between casing 109 and the pulsed gas-discharge lamp 107 may heat up due to substantially high thermal emissions from the tubular surface of the pulsed gas-discharge lamp 107, as about 40% of the input power may be transformed into heat in these applied modes, and its temperature may continue to increase rapidly. Experimental data shows that the wall temperature of the casing 109, the tube of the pulsed gas-discharge lamp 107, and the gas (air/ozone mixture) in the open space between these components may reach a quasi-stationary value even after 40 to 80 seconds from the actual beginning of working.

Heating up the air/ozone mixture in the space between the casing 109 and the tube of the pulsed gas-discharge lamp 107 may activate two simultaneous processes: first, at a high temperature (for example, more than 200° C.), ozone quickly decomposes into oxygen atoms, and immediately adopts a molecular form; and second, due to reduced gas density (air/ozone mixture) when this mixture is warmed up, there is a considerable difference between the density and the pressure inside and outside the casing 109. This may cause an ascending convective air (air/ozone mixture) stream to appear inside the casing 109 from the lower level orifices to the upper level orifices due to that natural draft effect. This ascending flow of warm air, where ozone has already been restored to oxygen molecules, may carry away all excess heat, cool the pulsed gas-discharge lamp 107 through natural convection, and exit the casing 109 practically free of ozone.

The interrelation between the indicated processes is reflected in the aforementioned Ratio (1) between the geometrical parameters of the casing 109 and operating modes of the pulsed gas-discharge lamp 107. The experimentally defined power correlation coefficient A can be values ranging from $2 \cdot 10^{13}$ to $3 \cdot 10^{14}$ $J^2/m^5 s^2$. Therefore, the following may be established and provided for within this range of values for A: an optimum balance between intensive emission of ultra-violet and visible radiation from the ultra-violet radiation source, generation of a considerable amount of heat in the air/ozone mixture, and the convective cooling of the tubular surface of the pulsed gas-discharge lamp 107 by the air flow caused by the natural draft on the other hand. In this way, the lower value of factor A may correspond to attaining high temperatures of the ozone intensive pyrolytic decomposition, whereas the higher value corresponds to temperature limits for the lamp bulb walls, softening the pulsed gas-discharge lamp 107 owing to excess heating.

Increasing the power supplied to the pulsed gas-discharge lamp 107 may cause more ultra-violet radiation to be produced. This, in turn, may result in: increased ozone generation inside the source of ultra-violet radiation, increased heat generation, increased the temperature of the air/ozone mixture, increased the speed of the ozone thermal decomposition, increased flow rate of air through the orifices in the casing 109, and better conditions for the convective cooling in the pulsed gas-discharge lamp 107.

Example 1

An air disinfection device 100 having 1 kW of power with a U-shaped pulsed gas-discharge lamp 107, positioned vertically, as shown in FIG. 1, in a quartz casing 9 that is 50 mm in diameter has the following technical parameters:

C=100 μF=$10^{-4}$ F, $U_0$=2,800 V, F=2.5 Hz, h=0.275 m, $S_{upper}$=$2 \cdot 10^{-4}$ $m^2$, $S_{lower}$=$1.7 \cdot 10^{-4}$ $m^2$.

The device 100 may be installed in the room of following dimensions: length of 3.70 m, width of 3.05 meters, height of 3.85 m, with a total surface area of the room of 29.2 $m^3$. Previously conducted microbiological tests with the disinfection device of these parameters showed that the device should work for 36 seconds in order to maintain efficient bactericidal air disinfection at 99.9% (i.e., 999 from every 1,0000 microorganisms are destroyed) in the room, measured for the *Staphylococcus Aureus* sanitary-indicative microorganism. The device was switched on by means of the program control unit 106 at the designated time, then the ozone level in the air was determined by a GANK-4 gas analyzer, the concentration of ozone in the air and the average volume concentration of ozone in the air were calculated. The later equaled to 49 μg/$m^3$. This value does not exceed the 100 μg/$m^3$ Maximum Allowable Concentration (MAC) of harmful substances permitted in the air in working zones of ozone in the air, in compliance with Sanitary-hygienic standard GN 2.2.5.1313-03.

Example 2

An air disinfection device 300 having 200 W of power with a pulsed gas-discharge lamp 307 in the form of a straight cylinder, positioned horizontally, as shown in FIG. 3, in a quartz casing 309 that is 20 mm in diameter has the following technical parameters:

C=60 μF=$6 \cdot 10^{-5}$ F, $U_0$=1,400 V, F=3.3 Hz, h=20 mm=0.02 m, $S_{upper}$=1 $cm^2$=$1 \cdot 10^{-4}$ $m^2$, $S_{lower}$=1 $cm^2$=$1 \cdot 10^{-4}$ $m^2$.

The device 300 may be installed in the same room with a total surface area of 29.2 $m^3$. According to microbiological tests to maintain efficient bactericidal air disinfection at 99.9%, measured for the *Staphylococcus Aureus* sanitary-indicative microorganism, this device should work for 300 seconds in order to achieve maximum results. The device was switched on by means of the program control unit 306 at the designated time, then, the average volume of ozone concentration in the air was calculated, which, in this case, was equal to 84 μg/m³. The received value would also not exceed the MAC of ozone permitted in the air in working zones.

While various embodiments have been described above, it should be understood that they have been presented by way of example only, and not limitation. Thus, the breadth and scope of a preferred embodiment should not be limited by any of the above described exemplary embodiments, but should be defined only in accordance with the claims and their equivalents for any patent that issues claiming priority from the present provisional patent application.

Various terms used herein have special meanings within the present technical field. Whether a particular term should be construed as such a "term of art," depends on the context in which that term is used. "Connected to," "in communication with," or other similar terms should generally be construed broadly to include situations both where communications and connections are direct between referenced elements or through one or more intermediaries between the referenced elements, including through the Internet or some other communicating network. "Network," "system," "environment," and other similar terms generally refer to networked computing systems that embody one or more aspects of the present disclosure. These and other terms are to be construed in light of the context in which they are used in the present disclosure and as those terms would be understood by one of ordinary skill in the art would understand those terms in the disclosed context. The above definitions are not exclusive of other meanings that might be imparted to those terms based on the disclosed context.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Brief Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. An air disinfection device comprising:
   a body, wherein the body houses:
      a power supply; and
      a control unit, wherein the control unit comprises a storage capacitor, a high-voltage DC power supply, an ignition pulse generator, a ferrite-core pulse transformer, and a program control unit; and
   an ultraviolet radiation source mounted on the body, wherein the ultraviolet radiation source comprises a pulse gas discharge lamp enclosed in a tubular cooled casing, the tubular cooled casing being translucent to bactericidal radiation;
   wherein the storage capacitor and the pulse gas discharge lamp form a discharge circuit connected to the ignition pulse generator through the ferrite-core pulse transformer;
   wherein the tubular cooled casing has one or more upper orifices defined through the tubular cooled casing and one or more lower orifices defined through the tubular cooled casing; and
   wherein convection air cooling capabilities provided by a natural draft is operable to be produced inside the tubular cooled casing.

2. The air disinfection device of claim 1, wherein the one or more upper orifices in the tubular cooled casing and the one or more lower orifices in the tubular cooled casing are separated by a distance h, based on the following ratio of parameters:

$$h \cdot \frac{S_{upper}^2 \cdot S_{lower}^2}{S_{upper}^2 + S_{lower}^2} = \frac{1}{A} \cdot C^2 U_0^4 F^2$$

wherein $S_{upper}$ is the total surface area of the one or more orifices in the upper level;
wherein $S_{lower}$ is the total surface area of the one or more orifices in the lower level;
wherein A is the power correlation coefficient;
wherein C is the capacitance of the storage capacitor;
wherein $U_0$ is the charge voltage of the storage capacitor; and
wherein F is the pulse repetition rate of the ignition pulse generator.

3. The air disinfection device of claim 1, wherein the ultraviolet radiation source is installed vertically on the body.

4. The air disinfection device of claim 3, wherein the pulse gas discharge lamp is U-shaped.

5. The air disinfection device of claim 1, wherein the ultraviolet radiation source is installed horizontally on the body.

6. The air disinfection device of claim 5, wherein the one or more lower level orifices are defined in a first lateral surface of the tubular cooled casing.

7. The air disinfection device of claim 6, wherein the one or more upper level orifices are defined in a second lateral surface of the tubular cooled casing.

8. The air disinfection device of claim 3, wherein the pulse gas discharge lamp is cylindrical.

* * * * *